(12) United States Patent
Heuscher et al.

(10) Patent No.: US 8,130,898 B2
(45) Date of Patent: Mar. 6, 2012

(54) PROSPECTIVE CARDIAC GATING IN COMPUTED TOMOGRAPHY

(75) Inventors: Dominic J. Heuscher, Aurora, OH (US); Stanislav Zabic, Highland Heights, OH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 208 days.

(21) Appl. No.: 12/738,738

(22) PCT Filed: Oct. 2, 2008

(86) PCT No.: PCT/IB2008/054031
§ 371 (c)(1),
(2), (4) Date: Apr. 19, 2010

(87) PCT Pub. No.: WO2009/056999
PCT Pub. Date: May 7, 2009

(65) Prior Publication Data
US 2010/0208863 A1     Aug. 19, 2010

Related U.S. Application Data

(60) Provisional application No. 60/983,907, filed on Oct. 30, 2007.

(51) Int. Cl.
*A61B 6/00* (2006.01)
(52) U.S. Cl. ............................................ 378/8; 600/428
(58) Field of Classification Search ................ 378/8, 62; 600/413, 425, 428
See application file for complete search history.

(56) References Cited

U.S. PATENT DOCUMENTS

| 6,526,117 | B1 | 2/2003 | Okerlund et al. |
| 7,042,976 | B2 | 5/2006 | Tsujii |
| 7,251,308 | B2 | 7/2007 | Tsuyuki |
| 2005/0113672 | A1 | 5/2005 | Salla et al. |
| 2005/0201509 | A1 | 9/2005 | Mostafavi et al. |
| 2007/0032735 | A1 | 2/2007 | Bruder et al. |
| 2009/0238327 | A1 | 9/2009 | Heuscher et al. |

FOREIGN PATENT DOCUMENTS

| EP | 1101444 A2 | 5/2001 |
| WO | 2004006771 A1 | 1/2004 |

OTHER PUBLICATIONS

Grass et al., Helical cardiac cone beam reconstruction using retrospective ECG gating, Physics in Medicine and Biology, 2003, 24 sheets, vol. 48.
Luhta, et al., A new 2D-tiled detector for multislice CT, Proceedings of SPIE, Medical Imaging 2006: Physics of Medical Imaging, Mar. 2, 2006, 12 sheets, vol. 6142.
Hsieh, et al., Step-and-shoot data acquisition and reconstruction for cardiac x-ray computed tomography, Medical Physics, Nov. 2006, pp. 4236-4248, vol. 33, No. 11.
Husmann, et al., Coronary Artery Motion and Cardiac Phases: Dependency on Heart Rate—Implications for CT Image Reconstruction, Radiology, Nov. 2007, pp. 567-576, vol. 245, No. 2.

*Primary Examiner* — Courtney Thomas

(57) ABSTRACT

A computed tomography scanner (10) acquires prospectively gated cardiac projection data. A scan controller (42) causes the scanner (10) to acquire projection data at the predicted location of a target cardiac phase in a cardiac cycle of the patient. An error determiner (44) determines an error between the target phase and the phase at which the projection data was actually acquired. Depending on the error, the patient is rescanned in a subsequent cardiac cycle.

20 Claims, 3 Drawing Sheets

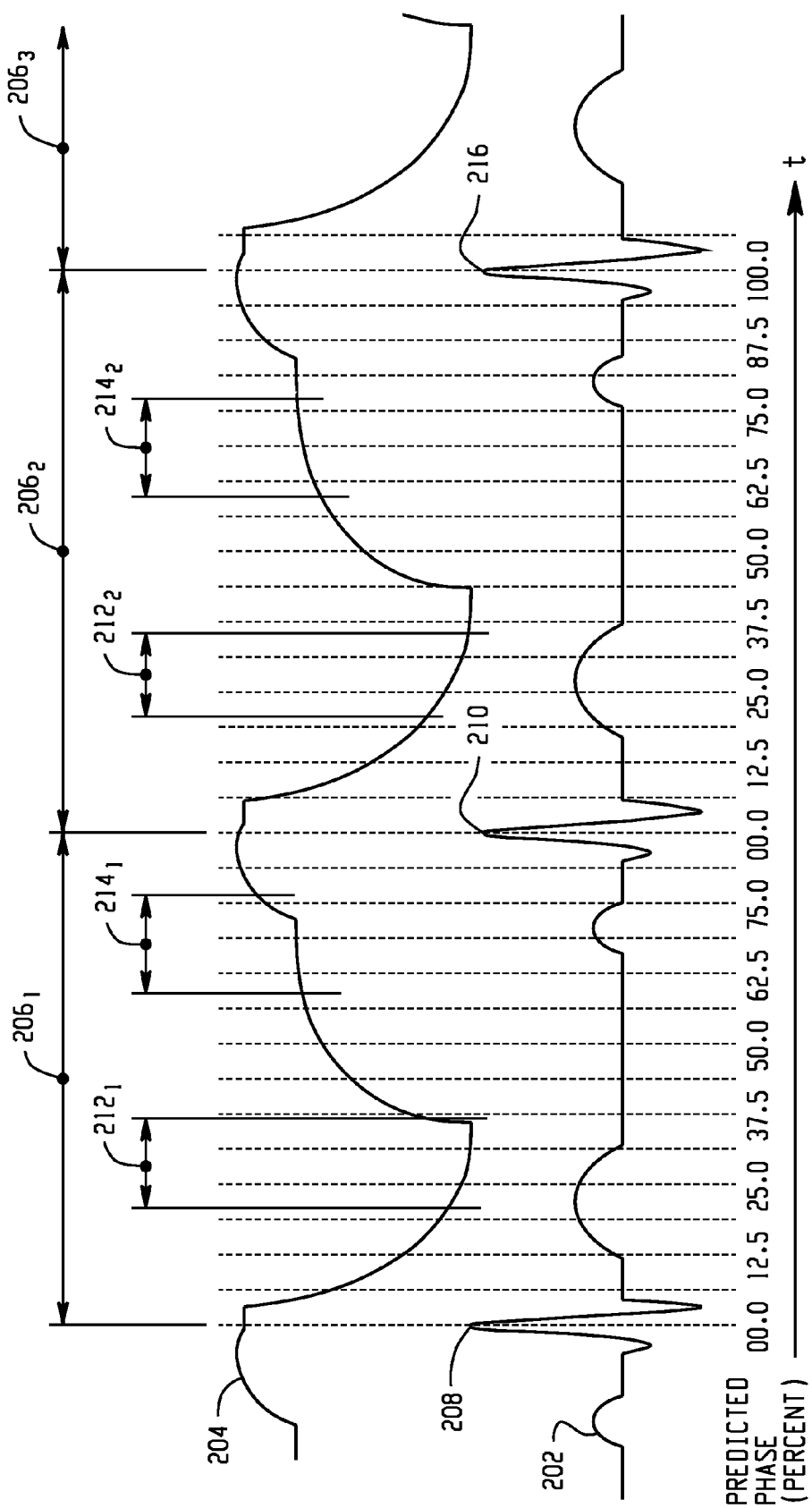

PROSPECTIVE CARDIAC GATING IN COMPUTED TOMOGRAPHY

CROSS REFERENCE TO RELATED APPLICATIONS

Figure 1:
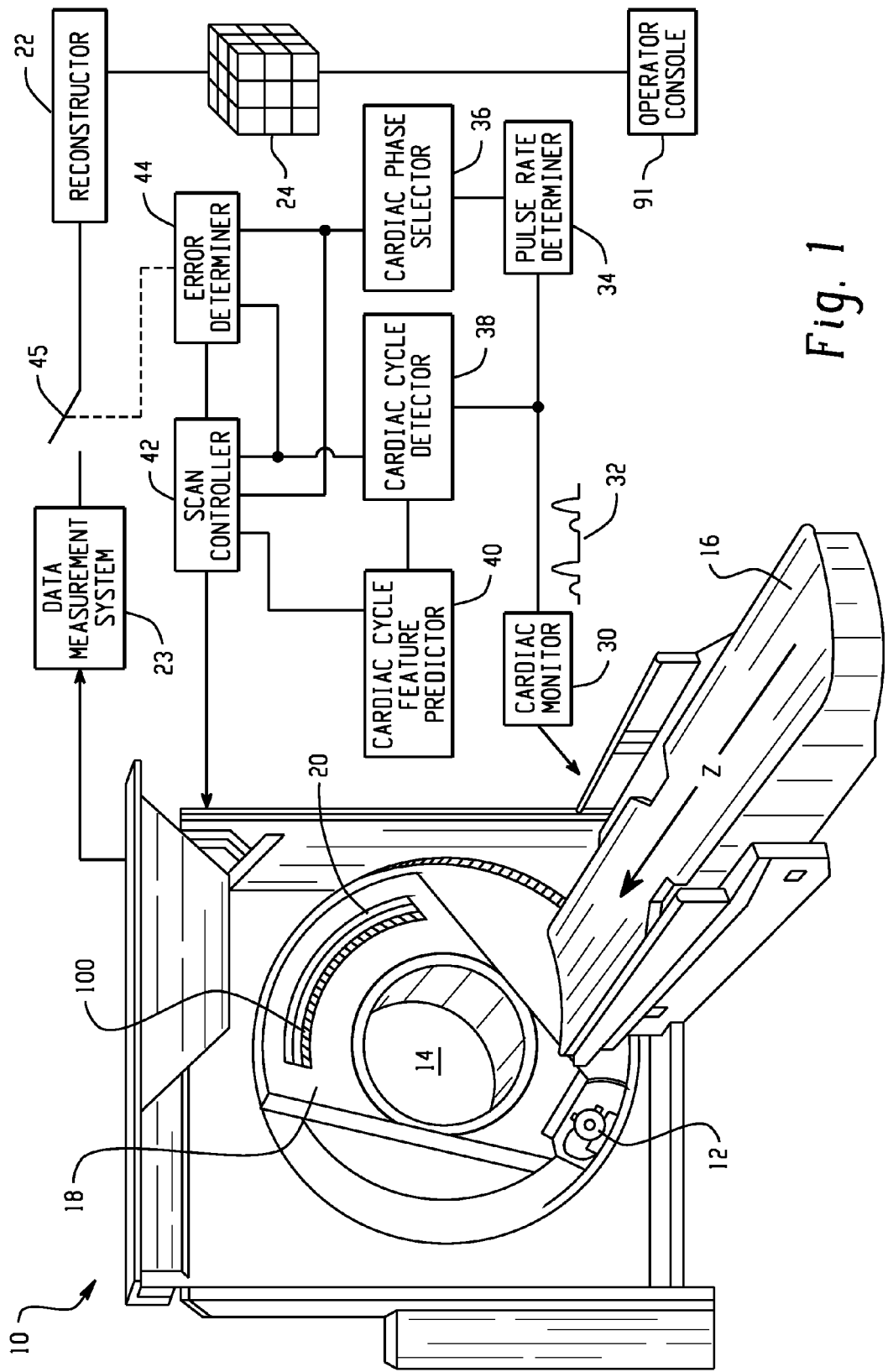

This application claims the benefit of U.S. provisional application Ser. No. 60/983,807 filed Oct. 30, 2007, which is incorporated herein by reference.

The present application relates to cardiac computed tomography.

Computed tomography (CT) has gained widespread acceptance as a medical imaging modality. One challenge, however, has been the imaging of moving objects. In cardiac CT, for example, the motion of the beating heart can introduce motion artifacts in the reconstructed images.

Cardiac CT has been performed using both retrospective and cardiac gating techniques. In retrospective gating, data acquired during a single low pitch helical scan has been used to generate images indicative of the object. See Grass et al., *Helical cardiac cone beam reconstruction using retrospective ECG Gating*, Phys. Med. Biol. 48 3069-3084 (2003). Multiple prospectively gated axial scans have also been used to cover the necessary anatomy. See Hseih, et al., *Step-and-shoot data acquisition and reconstruction for cardiac x-ray computed tomography*, Medical Physics 33(11): 4236-4248 (2006). For a significant number of patients, however, having to scan over multiple heart beats leads to compromised image quality. Therefore, the trend in the future will be to utilize large area detectors that allow scanning of the whole heart within a single heartbeat. See Luhta, et al., *A new 2D-tiled detector for multislice CT*, Proceedings of SPIE Vol. 6142 (2006).

These scans will be faster, with less motion artifacts, and lower dose, but will require prospective ECG-gating to capture the desired phase of the cardiac cycle. In applications such as CT angiography (CTA), the desired phase is ordinarily the phase in which there is as little cardiac motion as possible. For low heart rates, this quiescent phase occurs during the diastolic phase, while for high heart rates the quiescent phase occurs during the systolic phase. See Husmann, et al., *Coronary Artery Motion and Cardiac Phases: Dependency on Heart Rate—Implications for CT Image Reconstruction*, Radiology: Vol. 245: Number 2 (2007).

Gating accuracy is, however, influenced by a number of factors. One factor is the reliability of the cardiac cycle (e.g., R-wave) detection algorithms. Another factor is the repeatability of cardiac motion between successive heart beats. Still a third factor is the predictability of the patient's cardiac cycle.

Aspects of the present invention address these matters, and others.

According to a first aspect, an apparatus includes a cardiac cycle feature predictor that predicts the temporal location of a feature of the cardiac cycle of a patient, a scan controller that uses a measured temporal location of the feature of the patient's cardiac cycle and the predicted temporal location to cause a computed tomography scanner to acquire first prospectively gated projection data sufficient to reconstruct image-space data indicative of a region of the heart at a predicted quiescent phase of a first cardiac cycle of the patient, an error identifier that identifies an error between the phase at which the projection data was acquired and the quiescent phase. Depending on the identified error, the scan controller causes the scanner to acquire a second prospectively gated projection data at a predicted quiescent phase of a second cardiac cycle of the patient that is subsequent to the first cardiac cycle.

According to another aspect, a prospective cardiac gating method includes predicting the temporal location of a target cardiac phase in a first cardiac cycle of a patient, causing a computed tomography scanner to acquire gated projection data at the predicted temporal location of the target phase, determining an error between the phase at which the gated projection data was acquired and an actual temporal location of the target phase, and depending on the determined error, repeating the steps of predicting and causing for a second cardiac cycle.

According to another aspect, an apparatus includes a computed tomography scanner, means for predicting the temporal location of a feature of interest in the cardiac cycle of a patient, means for causing the computed tomography scanner to acquire first gated projection data that includes projection data sufficient to reconstruct image-space data indicative of a region of the patient's heart at the predicted temporal location of a target cardiac phase, and means for determining an error between the phase at which the first gated projection data was acquired and the target phase and rescanning the patient to acquire second projection data during a second cardiac cycle depending on the determined error.

Those skilled in the art will appreciate still other aspects of the present invention upon reading and understanding the attached figures and description.

FIGURES

Figure 2:
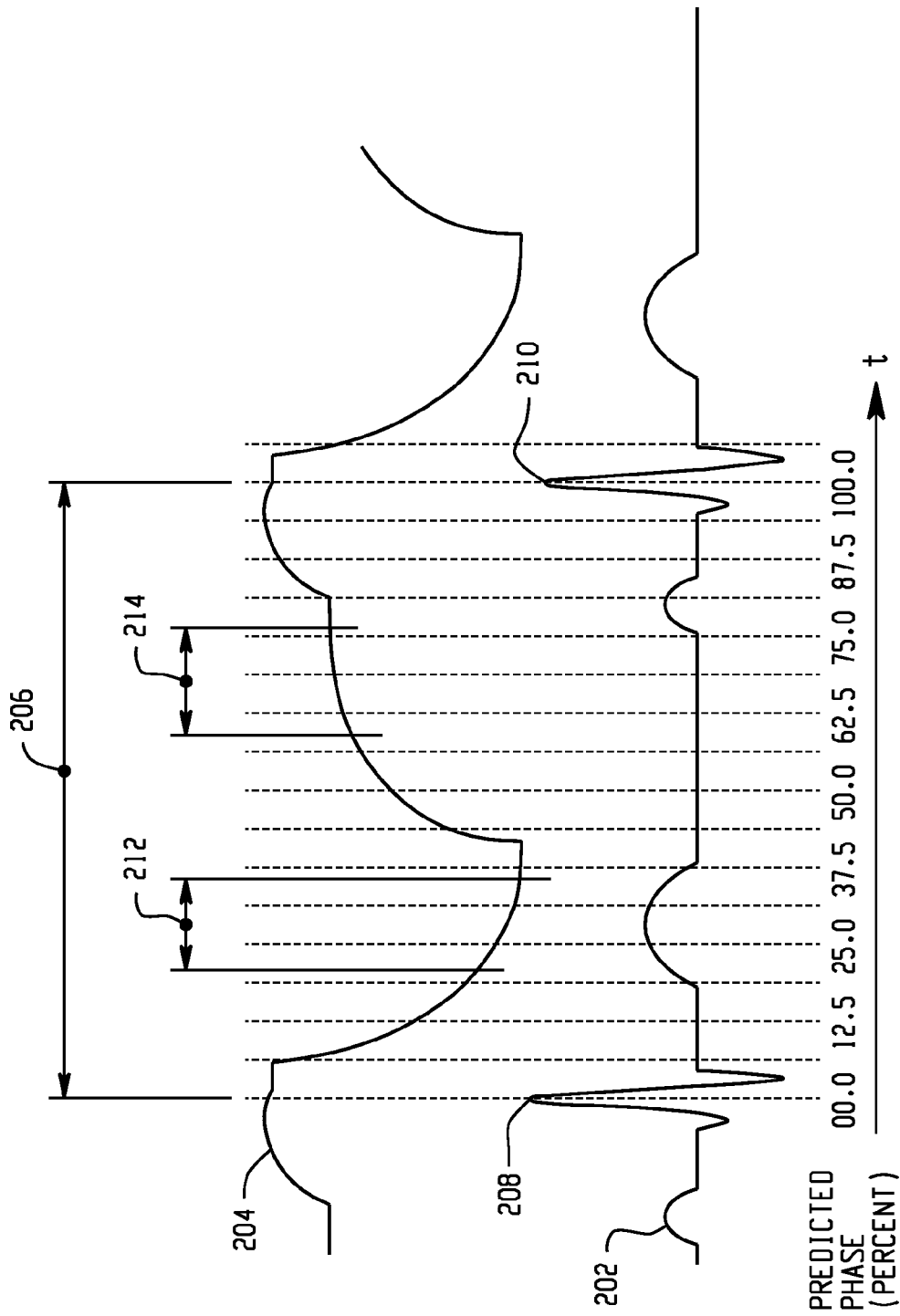

The present invention is illustrated by way of example and not limitation in the figures of the accompanying drawings, in which like references indicate similar elements and in which:

FIG. 1 depicts a CT scanner.
FIG. 2 depicts a cardiac cycle.
FIG. 3 depicts cardiac cycles.

With reference to FIG. 1, a CT scanner 10 includes a rotating gantry 18 which rotates about an examination region 14. The rotating gantry 18 supports an x-ray source 12 such as an x-ray tube. The gantry 18 also supports an x-ray sensitive detector 20 which subtends an arc on the opposite side of the examination region 14. X-rays produced by the x-ray source 12 traverse the examination region 14 and are detected by the detector 20. Accordingly, the scanner 10 generates scan data indicative of the radiation attenuation along a plurality of projections or rays through an object disposed in the examination region 14.

A support 16 such as a couch supports a patient or other object in the examination region 14. The support 16 is preferably movable in the longitudinal or z-direction.

The detector 20 includes a plurality of detector elements 100 disposed in an arcuate array extending in the transverse and longitudinal directions. In the case of a large area detector, the longitudinal extent of the detectors may be a significant fraction of the longitudinal dimension of a human heart. Depending on the configuration of the scanner 10 and the detector 20, the x-ray source 12 generates a generally fan, wedge, or cone shaped radiation beam that is approximately coextensive with the coverage of the detector 20.

Various scanning trajectories are contemplated. In a helical scan, relative movement of the patient and the x-ray source 12 are coordinated so that the x-ray source 12 and the detectors 20 traverse a generally helical path relative to the patient. In a circular or axial scan, the x-ray source 12, the relative axial positions of the support 16 and the gantry 18 remain fixed so that the x-ray source 12 and detectors 20 traverse a generally circular path. Note that the scanning orbit is preferably selected to acquire sufficient data to perform a 180 degree or other reconstruction of each voxel in a region of the heart during a single cardiac cycle.

In a fly-by scan, the x-ray source 12 generates a cone beam. In an initial phase, the x-ray source remains at a longitudinal position outside a region of interest while rotating, with no x-rays being emitted. In a ramp up phase, the longitudinal speed of the x-ray source 12 is accelerated or ramped up to a suitable scanning speed as the source 12 moves in the direction of the heart. Upon reaching a first longitudinal position at which the x-ray beam would traverse a first longitudinal end of the region of interest of the heart, the system enters a scanning phase. X-rays are emitted for a sampling period in which complete sampling for a 180 degree reconstruction for each voxel in the region of interest is obtained during a single cardiac cycle. Upon reaching the second longitudinal end of the region of interest, the x-rays are turned off. The longitudinal speed of the x-ray source is ramped down, and the longitudinal position of the x-ray source relative to the patient remains substantially fixed as the x-ray source 12 continues to rotate. Additional fly by scans may be repeated as desired, with the direction of longitudinal motion being alternated from scan to scan. Fly by scanning including suitable variations thereof is also described in commonly owned U.S. Patent Application No. 60/827,449, filed on Sep. 29, 2006 and entitled Fly-By Scanning, which application is expressly incorporated by reference in its entirety herein.

In this regard, it should be noted that the scan trajectory and angular sampling range are ordinarily selected to acquire sufficient data to reconstruct a region of interest of the heart over the course of a single heartbeat. In order to minimize the dose applied to the patient, the duration and angular sampling range are ideally selected so that the acquired data is essentially that needed to reconstruct the region of interest. The acquired data would thus include minimal or no "extra" data that would account for sampling phase errors such as those induced by irregularities in the patient's heartbeat relative to the predicted heartbeat.

A data measurement system 23 preferably located on or near the rotating gantry 18 receives signals originating from the various detector elements 100 and provides necessary analog to digital conversion, multiplexing, interface, data communication, and similar functionality. A reconstructor 22 reconstructs the projection data acquired by the data acquisition system 23 to generate volumetric- or image-space data 24 indicative of the interior anatomy of the patient.

A general purpose computer serves an operator console 91. The console 91 includes a human-readable output device such as a monitor or display and an input device such as a keyboard and mouse. Software resident on the console allows the operator to control the operation of the scanner by establishing desired scan protocols, initiating and terminating scans, viewing and otherwise manipulating the image-space data 24, and otherwise interacting with the scanner.

Also as illustrated, the system includes a cardiac monitor 30 such as an electrocardiogram (ECG) that produces cardiac data 32 indicative of the patient's cardiac cycle. A cardiac cycle detector 38 such as an R-wave detector processes the cardiac data 32 to identify an R-wave or other feature of interest, which serves to identify the beginning of or otherwise as a reference point in the cardiac cycle.

A pulse rate determiner 34 uses the cardiac data 32 to produce an output indicative of the patient's pulse rate.

A cardiac phase selector 36 uses the pulse rate information to select a target cardiac phase for scanning (i.e., to select a cardiac phase at which projection data should be acquired). In one implementation, the cardiac phase selector 36 compares the pulse rate to a threshold value, a suitable value of which is approximately eighty beats per minute (80 BPM). If the pulse rate is below the threshold value, scanning should ordinarily be conducted during systole; if above, scanning should ordinarily be conducted during diastole. In the case of systole, a suitable value of the target phase is in the neighborhood of thirty percent (30%) (i.e., a phase angle of about)108° relative to the R-wave; in the case of diastole a suitable value of the target phase is in the neighborhood of the seventy percent (70%).

A cardiac cycle feature predictor 40 uses the detected features to predict the temporal location of a feature of interest in the patient's cardiac cycle. Again to the example of an R-wave, the prediction may be made with reference to the predicted temporal location of an R-wave. Suitable prediction techniques will be described in further detail below. As will be appreciated, the predicted position can be used to predict the temporal location of the target phase in an upcoming cardiac cycle, for example by predicting the period of the cardiac cycle.

A scan controller 42 causes the scanner 10 to scan the patient at the predicted location of target cardiac phase. More specifically, the scan controller 42 uses the predicted temporal location of the cardiac phase and a signal indicative of a detected feature of interest to coordinate the timing of the scan to acquire prospectively gated projection data. For the purpose of the present discussion, it will be assumed that the timing is coordinated so that the temporal midpoint of the scan corresponds with the predicted location of the target cardiac phase, although other implementations are possible. Provided that the predicted location is accurate, the projection data should be acquired during a relatively quiescent portion of the cardiac cycle.

In some cases, however, it may turn out that the prediction was inaccurate. For example, a patient may experience an arrhythmia, irregular heartbeat, or other unpredicted event during the cardiac cycle in which the scan is being conducted, thereby disrupting the timing of the scan relative to the patient's cardiac cycle. As the disruption is likely to cause the projection data to be acquired during a relatively less quiescent portion of the cardiac cycle, the resultant image data will be relatively prone to motion artifacts.

Consequently, an error identifier 44 determines the error, if any, between the target cardiac phase and the phase at which the scan was actually conducted. If it is determined that the projection data was acquired at or within a desired tolerance of the selected phase, the projection data acquired during the scan is accepted and provided to the reconstructor 22 for reconstruction as indicated schematically by switch 45.

Various error determination techniques are contemplated. In one implementation, the error is determined with reference to the error in the predicted temporal location of the target cardiac phase. Again to the example in which the cardiac cycle detector 38 detects R-waves, the temporal distance between the R-waves that mark the beginning and end of the cardiac cycle (i.e., the RR interval), together with the scan timing data, may be used to determine the phase at which the data was actually acquired. The selected and actual phases are then compared. In another implementation, the error is determined with reference to an error in a cardiac cycle period prediction. In still another, the error is determined with reference to the error in the predicted temporal location of the feature of interest (e.g., the predicted time of the next R-wave).

If the error is greater than the desired tolerance, the scan controller 42 repeats the prediction and scanning process for the immediately subsequent or other subsequent cardiac cycle. Note that, in order to limit the dose applied to a given patient, the number of rescans may be limited, for example so that the total number of scans does not exceed three (3) or other suitable maximum. In such a case, the projection data acquired during the scan having the minimum scan phase error may be selected.

The foregoing will now be further described with reference to FIG. 2, which provides a schematic illustration of an ECG signal 202 and the left ventricular volume 204 as a function of time for an example cardiac cycle 206. For the purposes of the illustration, the cardiac cycle 206 is assumed to begin at the location of a first R-wave 208 and end at the location of a second R-wave 210, and represent a pulse rate of 80 BPM. A predicted phase within the cardiac cycle is also depicted, it being understood that the phase is calculated based on the measured and predicted locations of the first and second R-waves 208, 210, respectively. For the purposes of the present discussion, it will be assumed that cardiac cycle feature predictor 40 accurately predicted the location of the second R-wave 210 and that the temporal location of the target phase was predicted with accuracy.

As illustrated by the left ventricular volume curve 204, the cardiac cycle includes a first relatively quiescent period during systole in the neighborhood of the thirty percent (30%) phase point, which in the present example would be predicted to occur 225 milliseconds (ms) after the first R-wave. The cardiac cycle also includes second relatively quiescent period during diastole in the neighborhood of the seventy percent (70%) phase point, which in the present example would be predicted to occur 525 ms after the first R-wave. The approximate location of a scan having a duration of 150 ms and conducted at the predicted 30% phase point is depicted at 212; a the location of a similar scan conducted at the predicted 70% phase point is depicted at 214 (it being understood that only one such scan would normally be conducted in a given cardiac cycle). Assuming again that the location of the second R-wave 210 was accurately predicted, the scan phase error should be minimal.

As will be appreciated, there is in the present example some tolerance for error in the temporal location of the scan. The tolerance tends to increase if the scan time is relatively shorter. This may occur, for example, where the scanner 10 includes a large area or other detector having an axial field of view that is relatively large compared to the axial extent of the region of interest, or where the transverse extent of the region of interest is relatively limited. Likewise, the tolerance tends to increase as the pulse rate decreases, or if the presence of motion artifacts is relatively less important. In the present example, a tolerance in the neighborhood of about 50 mS would be suitable. Alternatively, the tolerance may be expressed as a fraction or percentage of the cardiac phase. Thus, if it is determined that the scan was actually conducted within the desired tolerance, the scan data may be accepted.

An example situation where an irregularity in the cardiac cycle leads to a prediction error is shown in FIG. 3. Curve 202 represents an ECG signal and curve 204 represents the left ventricular volume for first $206_1$ and second $206_2$ cardiac cycles. In the illustrated example, the second R-wave 210 occurred earlier than predicted. The period of the first cardiac cycle $206_1$ is thus relatively shorter than expected. As a consequence, the scans $212_1$, $214_1$ would be conducted relatively later than the target phase, in this example during a time at which the heart is non-quiescent (it again being appreciated that only a single scan 212, 214 would normally be conducted in a given cardiac cycle). Such a phase error would ordinarily be discovered by the error identifier 44, for example based on the measured temporal locations of the first 208 and second 210 R-waves.

Assuming that the error is outside the desired tolerance, the data from a scan $212_1$, $214_1$ conducted during the first cardiac cycle $206_1$ would not be accepted, and the prediction process would be repeated and the patient rescanned in the immediately subsequent cardiac cycle $206_2$. Such a rescan is indicated generally at $212_2$, $214_2$. If the temporal location of the third R-wave 316 was accurately predicted, the scan phase error should be minimal, thus leading to the acceptance of the projection data acquired during the rescan. If not, the prediction and rescanning process may be repeated as desired.

In this regard, it should be noted that the rescan need not be conducted in the immediately subsequent cardiac cycle $206_2$ and may instead be conducted during a still more subsequent cardiac cycle such as cardiac cycle $206_3$. Such an implementation is particularly attractive in situations where the target cardiac phase occurs in systole and it may not be possible to reposition the scanner 10 for the rescan in the time period between the second R-wave 210 and the selected cardiac phase. Such a situation is particularly likely to occur where the (re)scan is a fly-by scan. Note also that information from the intervening cardiac cycles(s) may be used in the phase prediction for the cardiac cycle in which the rescan is conducted.

Various prediction techniques will now be further described.

According to a first, known technique, the median of the measured time intervals between the n (e.g., where n=4) features of interest of the cardiac cycle immediately preceding the feature for which the location is to be predicted is used to predict the temporal location of the feature. Again to the R-wave example, the next cardiac cycle would be expected to have a period that is equal to the median RR interval of the n−1 (e.g., 3) preceding cardiac cycles.

A second technique is similar to the first technique, but employs a threshold. In one example, those cycle(s) having a period that falls outside of a threshold value may be disregarded. For example, those cardiac cycle(s) having a period that is significantly different from that of their neighbors are relatively likely to be aberrant. In another example, if the period of the most recent cardiac cycle falls within a threshold of the median, then the period of the most recent cardiac cycle is used to predict the temporal location of the feature. If not, then the median is used.

A third, known technique, is similar to the first technique, except that the mean value is used rather than the median value.

According to a fourth technique, a least squares linear fit of the intervals between the n (e.g., where n=5) preceding features of interest may be used to predict the location of the feature. Such a technique tends to account for trends such as increases or decreases in the pulse rate. Note that higher order fitting techniques may also be used.

According to a fifth technique, the fourth technique may be modified to include a threshold. More specifically, the location of the linear fit for the most recent cycle and the actual information for the most recent cycle are compared. If the linear fit falls outside the threshold, then the median of the most recent n cycles is used. One suitable threshold is on the order of 100 mS.

A sixth technique employs pattern matching to detect likely repeats or patterns in the patient's cardiac cycle and predicts the temporal location of an upcoming feature accordingly. In one example, the n preceding features of interest (e.g., where n=5) are searched to identify patterns such as a generally increasing (or decreasing) pulse rate and/or local peaks (or valleys) in the heart rate. If the most recent cardiac cycle matches a previous cycle, then a feature of interest from a cycle of the identified pattern is used to predict upcoming feature of interest. Matching can be determined, for example, with reference to the zero crossing value or the local minimum deviation from a value. If no matching cycle is found, the median value of the previous n (e.g., where n=3) cycles is used.

Such a technique can also be expressed as follows, where $RR_N$ is the period of the cardiac cycle in which the scan is to be conducted, N is the cycle for which the period is to be determined, and NR is the number of features of interest to be evaluated:

```
FOR i=3...NR+2
    S1=sign(RR_{N-2}- RR_{N-1}); S2=sign(RR_{N-i-1}- RR_{N-i})
    IF S1=S2 AND RR_{N-1} is between RR_{N-i-1} and RR_{N-i+1}
        THEN RR_N=RR_{N-i+1}; BREAK
    IF |RR_{N-i}- RR_{N-1}|<|RR_{N-i-1}- RR_{N-1}| AND
       |RR_{N-i}- RR_{N-1}|<|RR_{N-i+1}- RR_{N-1}|
        THEN RR_N=RR_{N-i+1}; BREAK
    OTHERWISE CONTINUE
IF i=NR+2
    THEN RR_N=median(RR_{N-i} | i=1...NR)
```

As discussed above, the prediction may be subject to error. Two methods of mitigating the prediction error were compared. The first method involves rescanning the patient immediately after determining that the predicted RR-interval is outside the desired range. The process is repeated for up to m scans as necessary. According to the second method, for the same average dose administered in the first technique, a single scan is extended to accommodate as much of the prediction error as possible.

The results summarize what percentage of patients would have been successfully scanned using the above two methods and how well a variety of prediction algorithms perform. Three groups were considered: lower heart rates using the diastolic phase as the target phase point; higher heart rates using the systolic phase as the target phase point; and all heart rates using both the systolic and diastolic phases as the desired points.

Cardiac spiral CT using 64-slice low pitch helical scans (Philips Brilliance 64) was performed on 245 patients whose ECG waveforms were used to detect the corresponding locations of the R-waves (called R-tags). Using these R-tags, different prediction algorithms could be compared including:
1) Median value of preceding n R-tags,
2) Median value of preceding n R-tags or last R-tag if within a threshold,
3) Mean value of preceding n R-tags,
4) Least squares (LS) linear fit of preceding n R-tags,
5) LS linear fit or median value of preceding n R-tags, dependent on threshold,
6) R-tag value after nearest value to last R-tag, The 30% and 70% phase points where predicted for 5 consecutive heart beats for each patient, for a total of 1225 predicted heart beats. The two scanning methods described above were compared in terms of the percentage of patients for which the desired phase point was predicted within a tolerance of 50 milliseconds. For the rescanning method 1, results were compared using a maximum m of 3 or 4 scans. The number n of preceding R-tags utilized for the above algorithms varied from 1 to 5. The results were divided into the following three groups:

1) Heart rates bellow 80 BPM and a target phase point of 70%.
2) Heart rates above 80 BPM and a target phase point of 30%.
3) Target phase points of both 30% and 70% for all patients.

To begin with, 88% of the patients (215 in total, all of whom had some form of beta-blocker) had a heart rate below 80 BPM. Heart rates ranged from 38 BPM with an overall average heart rate of 65 BPM. For the 88% whose heart rate was bellow 80 BPM, the following table shows the percentage of patients whose phase point was successfully predicted using the various algorithms and scan method 1:

|  | Algorithm | | | | | |
| --- | --- | --- | --- | --- | --- | --- |
|  | #1 | #2 | #3 | #4 | #5 | #6 |
| % Patients | 94 | 92 | 92 | 93 | 93 | 97 |
|  | n = 3 gave the best results | n = 3 16% threshold | n = 3 | n = 5 | n = 5 100 ms threshold | n = 5 |
| Avg. Scans m = 3 max | 1.29 | 1.25 | 1.31 | 1.31 | 1.3 | 1.25 |

The relative performance of the predictors was the same for all groups and scan modes with algorithm #6 performing the best throughout.

The relative performance of the two methods of scanning for heart rates bellow 80 BPM was as follows (the 70% phase point and predictor algorithm #1 were used):

| Scan method | #1 | #2 |
| --- | --- | --- |
| % Patients (n = 3) | 94 | 88 |
| Average scans (m = 3 max) | 1.29 | |
| Corresponding revolutions | | 0.9 |

The relative performance of the two methods of scanning for heart rates above 80 BPM was as follows (the 30% phase point and the predictor algorithm #1 were used):

| Scan method | #1 | #2 |
| --- | --- | --- |
| % Patients (n = 3) | 97 | 93 |
| Average scans (m = 3 max) | 1.19 | |
| Corresponding revolutions | | 0.8 |

Finally, the relative performance of the two methods of scanning using both the 30% and 70% phase points (for all heart rates) was as follows (algorithm #1 was used as the predictor):

| Scan method | #1 | #2 |
|---|---|---|
| % Patients (n = 3) | 94 | 88 |
| Average scans (m = 3 max) | 1.28 | |
| Corresponding revolutions | | 0.9 |

In general, all the predictor algorithms performed comparably with algorithm 6 performing the best throughout. Perhaps most surprisingly, the best scan method was to rescan the patient as necessary as opposed to extending a single scan.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. An apparatus comprising:
a cardiac cycle feature predictor that predicts a temporal location of a feature of a cardiac cycle of a patient;
a scan controller that uses a measured temporal location of the feature of the cardiac cycle of the patient and the predicted temporal location to cause a computed tomography scanner to acquire first prospectively gated projection data sufficient to reconstruct image-space data indicative of a region of the heart at a predicted quiescent phase of a first cardiac cycle of the patient; and
an error identifier that identifies an error between a phase at which the projection data was acquired and the quiescent phase;
wherein, depending on the identified error, the scan controller causes the scanner to acquire second prospectively gated projection data at a predicted quiescent phase of a second cardiac cycle of the patient that is subsequent to the first cardiac cycle.

2. The apparatus of claim 1 wherein the first projection data consists essentially of projection data acquired over a range of angles necessary to reconstruct the image-space data.

3. The apparatus of claim 1 wherein the scan controller causes the computed tomography scanner to acquire the first projection data in a fly by scan.

4. The apparatus of claim 1 wherein the second cardiac cycle is immediately subsequent to the first cardiac cycle.

5. The apparatus of claim 1 including a cardiac phase selector that selects a target cardiac phase as a function of a pulse rate of the patient, wherein the predicted quiescent phase of the first cardiac cycle is a predicted temporal location of the target cardiac phase.

6. The apparatus of claim 5 wherein the cardiac phase selector selects a target phase in systole if the pulse rate is greater than a first value and a target phase in diastole if the pulse rate is less than the first value.

7. The apparatus of claim 1 including a cardiac phase selector that selects a target cardiac phase, wherein the predicted quiescent phase of the first cardiac cycle is a predicted temporal location of the target phase, and wherein the second cardiac cycle is immediately subsequent the first cardiac cycle if the target cardiac phase is in diastole and other than immediately subsequent the first cardiac phase if the target cardiac phase is in systole.

8. The apparatus of claim 1 wherein the predicted location of the feature is determined using a technique that includes examining a plurality of cardiac cycles of the patient to identify a pattern present therein and identifying a likely repetition of the pattern.

9. The apparatus of claim 8 wherein the technique includes identifying a zero-crossing value or a local minimum deviation.

10. A prospective cardiac gating method comprising:
predicting a temporal location of a target cardiac phase in a first cardiac cycle of a patient;
causing a computed tomography scanner to acquire gated projection data at the predicted temporal location of the target cardiac phase;
determining an error between a phase at which the gated projection data was acquired and an actual temporal location of the target phase;
depending on the determined error, repeating the steps of predicting and causing for a second cardiac cycle.

11. The method of claim 10 wherein predicting includes using a matching technique to identify a match between a third cardiac cycle that immediately precedes the first cardiac cycle and a fourth cardiac cycle that precedes the third cardiac cycle.

12. The method of claim 11 including, if a matching cardiac cycle is not identified, using a second, different technique to predict a period of the first cardiac cycle.

13. The method of claim 10 wherein the repeating the predicting and the causing for the second cardiac cycle depending on the determined error includes not repeating the causing.

14. The method of claim 10 wherein the causing includes causing the scanner to acquire cone beam projection data over an angular range that is essentially limited to a range of projection angles needed to reconstruct the patient's heart.

15. The method of claim 10 wherein the causing includes causing the scanner to perform an axial scan.

16. The method of clam 10 wherein the causing includes causing the scanner to perform a fly by scan.

17. The method of claim 10 wherein the determining includes determining an error in a predicted period of the first cardiac cycle, an error in a predicted temporal location of a feature of the first cardiac cycle, or an error between the predicted location of the target cardiac phase and an actual location of the quiescent cardiac phase.

18. The method of claim 10 including rejecting the projection data acquired in the first cardiac cycle and reconstructing the projection data acquired in the second cardiac cycle.

19. The method of claim 10 wherein the second cardiac cycle is a cardiac cycle following the first cardiac cycle.

20. An apparatus comprising:
a computed tomography scanner;
means for predicting a temporal location of a feature of interest in a cardiac cycle of a patient;
means for causing the computed tomography scanner to acquire first gated projection data that includes projection data sufficient to reconstruct image-space data indicative of a region of a heart of the patient's at a predicted temporal location of a target phase in a first cardiac cycle of the patient;
means for determining an error between a phase at which the first gated projection data was acquired and an actual location of the target phase and rescanning the patient during a second cardiac cycle to acquire second gated projection data depending on the determined error.

* * * * *